United States Patent
Zeraatkar et al.

(10) Patent No.: US 9,753,147 B2
(45) Date of Patent: Sep. 5, 2017

(54) DESKTOP OPEN-GANTRY SPECT IMAGING SYSTEM

(71) Applicant: Parto Negar Persia Co., Tehran OT (IR)

(72) Inventors: Navid Zeraatkar, Tehran (IR); Mohammad Hossein Farahani, Tehran (IR); Mohammad Reza Ay, Tehran (IR); Saeid Sarkar, Tehran (IR)

(73) Assignee: Parto Negar Persia Co., Tehran (IR)

( * ) Notice: Subject to any disclaimer, the term of this patent is extended or adjusted under 35 U.S.C. 154(b) by 0 days.

(21) Appl. No.: 14/975,772

(22) Filed: Dec. 19, 2015

(65) Prior Publication Data

US 2016/0116604 A1 Apr. 28, 2016

Related U.S. Application Data

(60) Provisional application No. 62/146,350, filed on Apr. 12, 2015.

(51) Int. Cl.
 *G01T 1/164* (2006.01)
 *A61B 6/03* (2006.01)
 *G21K 1/02* (2006.01)
 *A61B 6/06* (2006.01)
 *A61B 6/00* (2006.01)

(52) U.S. Cl.
 CPC .......... *G01T 1/1648* (2013.01); *A61B 6/037* (2013.01); *A61B 6/06* (2013.01); *A61B 6/4208* (2013.01); *A61B 6/44* (2013.01); *A61B 6/508* (2013.01); *G21K 1/02* (2013.01)

(58) Field of Classification Search
 CPC ......... A61B 6/037; A61B 6/06; A61B 6/4208; A61B 6/44; A61B 6/508; G01T 1/1648; G21K 1/02
 See application file for complete search history.

(56) References Cited

U.S. PATENT DOCUMENTS

| | | | | |
|---|---|---|---|---|
| 5,001,347 A | * | 3/1991 | Hsieh | G01T 1/1648 250/363.1 |
| 5,523,571 A | * | 6/1996 | Velazquez | G01T 1/1648 250/363.05 |
| 5,825,031 A | | 10/1998 | Wong et al. | |

(Continued)

FOREIGN PATENT DOCUMENTS

WO    WO 02089660 A2  *  11/2002  ........... G01T 1/1644

OTHER PUBLICATIONS

Christian Lackas, T-SPECT: a novel imaging technique for small animal research, Nuclear Science, IEEE Transactions on, Feb. 2005, vol. 52, Issue 1, pp. 181-187.

(Continued)

*Primary Examiner* — Mark R Gaworecki
(74) *Attorney, Agent, or Firm* — NovoTechIP International PLLC

(57) ABSTRACT

An open-gantry structure of SPECT imaging system for scanning human small organs or small animals and method for preparing the system is disclosed. The system contains an imaging desk that one or multiple detector heads are rotated around the object to be scanned while tilted under the imaging desk and dedicated image reconstruction algorithm was developed for the system in case of applying single pinhole collimator.

20 Claims, 10 Drawing Sheets

(56) References Cited

U.S. PATENT DOCUMENTS

| | | | |
|---|---|---|---|
| 5,866,906 A * | 2/1999 | Jensen | G01T 1/1648 250/363.05 |
| 6,590,214 B1 | 7/2003 | Karmalawy | |
| 7,209,579 B1 | 4/2007 | Weisenberger et al. | |
| 7,332,722 B1 | 2/2008 | Tran et al. | |
| 8,462,911 B2 | 6/2013 | Vesel et al. | |

OTHER PUBLICATIONS

Frans Van Der Have, U-SPECT-II: an ultra-high-resolution device for molecular small-animal imaging, Journal of Nuclear Medicine, Apr. 2009, vol. 50, No. 4, pp. 599-605.

Philips nuclear camera, http://www.ais-nuclear.com/nuclear-medicine-cameras/reconditioned-nuclear-medicine-cameras/philips-nuclear-camera, Apr. 24, 2014.

GE Healthcare SMV DST-XLi, http://www.medwrench.com/?equipment.view/equipmentNo/3526/GE-Healthcare/SMV-DST-XLi, Dec. 18, 2015.

\* cited by examiner

DESKTOP OPEN-GANTRY SPECT IMAGING SYSTEM

CROSS REFERENCE TO RELATED APPLICATION

This application claims the benefit of priority from U.S. Provisional Patent Application Ser. No. 62/146,350, filed on Apr. 12, 2015, and entitled "Desktop Open-Gantry SPECT Imaging System Using Tilted Detector," which is incorporated by reference herein in its entirety.

SPONSORSHIP STATEMENT

This application has been sponsored by the Iranian Nanotechnology Initiative Council, which does not have any rights in this application.

TECHNICAL FIELD

The present application generally relates to the design of a SPECT imaging system for scanning small animal and the human organs, and more specifically to the development of a dedicated image reconstruction algorithm to generate 3-dimensional map of activity concentration using acquired projection data.

BACKGROUND

Regarding the highlighted role of molecular imaging in pre-clinical imaging, much effort have been devoted to development of high performance single-photon emission computed tomography (hereinafter "SPECT") imaging systems. Different SPECT imaging systems have been reported in the art, in which the object to be imaged is placed in a closed gantry and a set of collimator-detector is rotated around it. Closed gantry of the systems, and difficult monitoring of the object are known drawbacks of the systems disclosed in the prior art. Moreover, high production cost and low tomographic spatial resolution, are among other negative aspects of SPECT systems reported in prior art.

Therefore, there is a need to address the issues of closed gantry structures, complexity of the systems, and their expensiveness.

SUMMARY

In one general aspect, the application describes a new system for single-photon emission computed tomography (SPECT) imaging. The system has open-gantry structure and contains an imaging desk and at least one head. The head is located underneath the imaging desk with a tilt angle from the hypothetical plane of the desk. The head rotates around an axis of rotation, which is perpendicular to the imaging desk plane and passing the center of the desk, for data acquisition.

In the system introduced in this application, the head contains a collimator and a detector. The collimator could be selected from different types of collimators. In one implementation, the pinhole collimator may be used in the system.

The detector can be selected from various types of detectors, including: simple monolithic scintillation crystal coupled to Photomultiplier Tubes (PMTs), a pixelated scintillating crystal coupled to Position-Sensitive PMTs (PSP-MTs), a monolithic/pixelated crystal coupled to photo-diodes, a solid-state detector, etc. In one implementation, a monolithic scintillation crystal coupled to PMTs may be used in the system.

In another aspect of the present application, a method for data acquisition is introduced, which comprises: placing an object to be imaged in a dedicated place on an imaging desk; rotating at least one head around the object while the head is tilted underneath the imaging desk; acquiring some projection views; and storing the projection views.

BRIEF DESCRIPTION OF THE DRAWINGS

This application will be understood more clearly from the following description and the accompanying figures. These figures are given purely by way of an indication and in no way restrict the scope of the application. Of these figures:

FIG. 2A illustrates an object to be imaged, the imaging desk, the head containing pinhole collimator, the detector and the shielding layer where the head rotates around the object while tilted under the imaging desk. FIG. 2B is similar to FIG. 2A, albeit with scintillator crystal and Photomultiplier Tubes used in detector together with the rotation path of the head for data acquisition.

DETAILED DESCRIPTION

The following detailed description is presented to enable any person skilled in the art to make and use the teachings of the instant application. For purposes of explanation, specific nomenclature is set forth to provide a thorough understanding of the present application. However, it will be apparent to one skilled in the art that these specific details are not required to practice the teachings of the instant application. Descriptions of specific applications are provided only as representative examples. Various modifications to the described implementations will be readily apparent to one skilled in the art, and the general principles defined herein may be applied to other implementations and applications without departing from the scope of the present application. The present application is not intended to be limited to the implementations shown, but is to be accorded the widest possible scope consistent with the principles and features disclosed herein.

In contrast to the SPECT method in the art, in which one or multiple heads are mounted on a rotating, closed-gantry, which rotates around an object to be imaged for data acquisition, the system according to the present application has a desktop open-gantry structure, where the heads rotate around the object, while they are tilted underneath an imaging desk. The instant application allows for multiple 2-D images to be taken from different angles then by using a SPECT computer program a 3-D image is produced. In the instant application, the open-gantry feature, enables the operator to monitor the object easily. Compared to closed-gantry counterparts, open-gantry is a low production-cost method and has higher tomographic spatial resolution.

Figure 1:
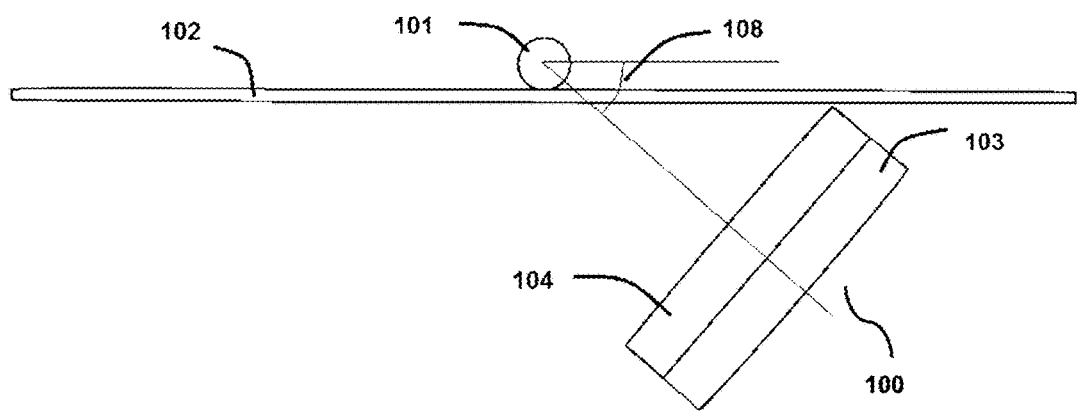
FIG. 1 is a general side view of an SPECT imaging system in accordance with an exemplary and non-limiting implementation, which illustrates a head that contains a detector and a collimator, which rotates around the object to be imaged, while tilted under an imagining desk.

FIG. 1 of the drawings shows a general view of an imaging system according to one implementation, which includes an imaging desk 102 and one head 100 containing a detector 103 and a collimator 104. The head(s) can rotate accurately using a motor (some motors) which in turn are controlled precisely using a controller. The imaging desk 102 is configured to provide a place for laying the object 101.

The dedicated area of the imaging desk 102 where the object 101 is placed on, may be better to be made of materials with low attenuation against emitted photons (e.g. carbon fiber). The other parts of the imaging desk may be made of any kind of material.

FIG. 1 of the DRAWINGS also illustrates the tilt angle 108, which can be adjusted to get better image quality. The head(s) should maintain a tilt angle 108, while rotating around the object 101. Changing the tilt angle 108 may affect the shape of field-of-view (FOV) as well as image quality parameters, such as tomographic spatial resolution, contrast, noise, uniformity, etc.

In some implementations of the present application, some parts or the whole object 101 could be placed beneath the imaging desk 102 through a hole or opening or an aperture. One or multiple heads could be implemented in the imaging system of the present application. Using of more heads increases the detection efficiency. Therefore, with the same administered radiation dose, total scan time can get shorter or at the same total scan time, the smaller amount of administered radiation dose can be applied. Any kind of collimator can be used for the imaging system of the present application e.g. parallel-hole, pinhole, multi-pinhole, etc. However, the image reconstruction algorithm alters depending on the type of the collimator used.

Figure 2A:
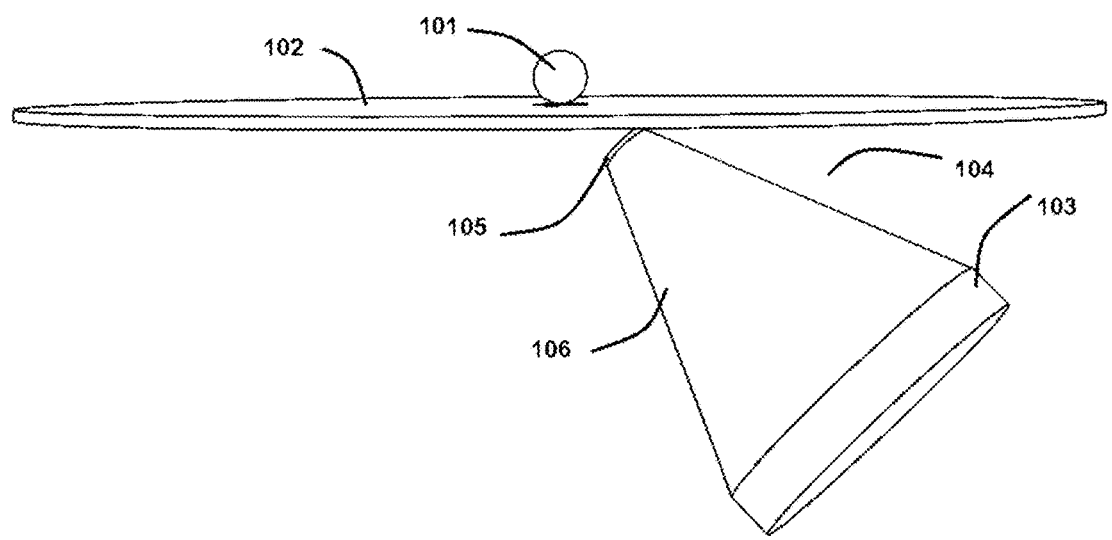
FIG. 2A and FIG. 2B are prospective side views of a SPECT imaging system in accordance with a non-limiting implementation of the present application.

FIG. 2A of the drawings illustrates one implementation of the present application where a pinhole collimation 105 with double knife-edge structure is used to provide both high resolution and appropriate sensitivity for the required field-of-view (FOV). A shielding layer 106 of a high-attenuation material, such as lead, is appropriate to be implemented to prevent scattered and unwanted photons to reach the detector. The collimator can be made of different materials such as lead, tungsten, gold, etc. To provide appropriate attenuation in one implementation of the present application, tungsten is used as the collimator material.

The detector 103 used in the head can be, for example a simple monolithic scintillation crystal coupled to Photomultiplier Tubes (PMTs), a pixelated scintillating crystal coupled to Position-Sensitive PMTs (PSPMTs), a monolithic/pixelated crystal coupled to photodiodes, a solid-state detector, etc.

Figure 2B:
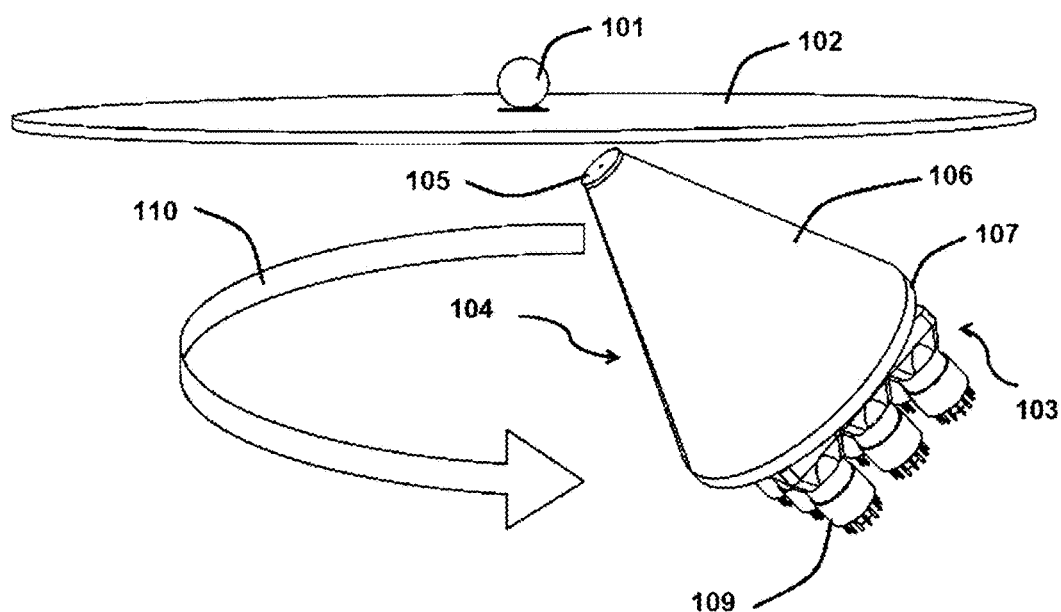

In one implementation of the present application as illustrated in FIG. 2B of the drawings, a monolithic scintillation crystal 107 is coupled to ordinary PMTs 109, which has the lowest cost among all kind of detectors. A scintillator is a material that has the ability to absorb a photon and convert that energy into light. Scintillators are used to detect the energy given off by a radioactive isotope. The crystal has similar properties to ones used in clinical SPECT/gamma camera systems. Any kind of read-out electronics can be used. The wide arrow 110 in FIG. 2B depicts the rotation path of the collimator/detector set for data acquisition. As shown, the rotation path of the collimator/detector is in a plane that is parallel to the plane in which the imaging desk is located. In this specific example, the plane is shown to be a horizontal plane. Alternatively, the plane may be a vertical plane or plane in other directions. To illustrate further, assuming there is an imaginary vertical axis passing through the center of the imaging desk, then the collimator/detector rotates around the imaginary vertical axis while located beneath the imaging desk.

The characteristics of the crystal and detector used in the present application are summarized and set forth in TABLE 1. As a widely available and also cheap scintillator, sodium iodide thallium-activated (NaI(Tl)) scintillator crystal was used in this implementation. The size of the crystal was set as 30 cm (W)×30 cm (L)×⅜" (thickness).

TABLE 1

The characteristics of the detector used for the system.

| | |
|---|---|
| Material | sodium iodide thallium-activated (NaI(Tl)) |
| Dimensions | 30 cm × 30 cm × ⅜" |
| Energy Resolution | 10% at 140 keV |
| Intrinsic Spatial Resolution | 3 mm |
| Energy Window | 125-155 keV |

Figure 3:
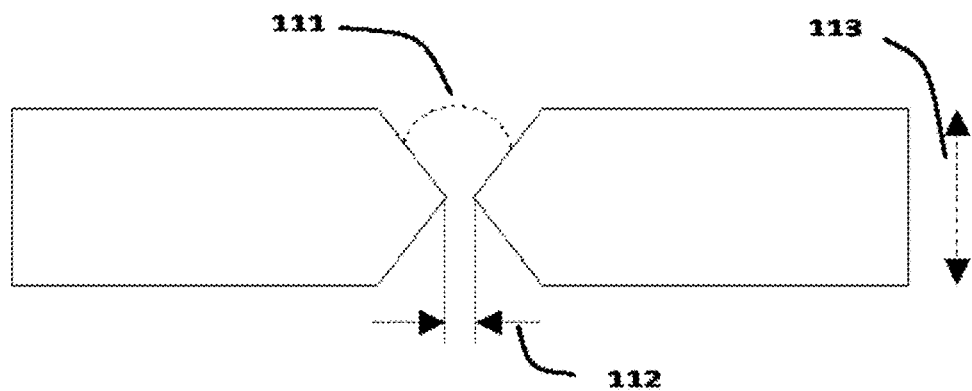
FIG. 3 is a cross section of double knife-edge structure of the pinhole collimator used as an example design for the collimator.

FIG. 3 of the DRAWINGS illustrates a cross sectional view of the double knife-edge structure of the applied pinhole collimator. Pinhole collimator consists of a dense material with a single small hole drilled in the middle. It offers the benefit of high magnification of a single object. Based on the needed spatial resolution and sensitivity, the pinhole 112 can have different diameters; larger pinhole 112 diameters result in a lower spatial resolution and a higher geometric efficiency. For the present application as an implementation, a pinhole with a diameter of 1 mm was applied.

The opening angle 111 of the pinhole as illustrated in FIG. 3 affects image quality including spatial resolution, geometric efficiency, and Field-of-View (FOV). Wider opening angles 111 lead to lower spatial resolution, higher geometric efficiency and larger FOV. For example, in one implementation of the present application, an opening angle of about 56° is used.

With another reference to FIG. 3 of the DRAWINGS, when collimator thickness 113 is larger, less undesirable photons pass the collimator. Although thicker collimator results in higher prevention ability for the unwanted photons, heavier collimator, larger size, and more fabrication expense are some drawbacks of it. In some implementation of the present application, a 5 mm-thick collimator leads to an attenuation factor of about $10^{-8}$ for undesirable photons.

The geometric spatial resolution (denoted by $R_g$), magnification at the center of image matrix (denoted by letter m), total spatial resolution (denoted by $R_o$), and geometric efficiency (denoted by letter E) at distance D from the pinhole and angle θ from the normal vector of the collimator, as is known in the art, can be calculated using the equations set forth herein below:

$$R_g = \frac{po + pd}{pd} \times d$$

$$m = \frac{pd}{po}$$

$$R_o = \sqrt{(R_g^2 + (R_i/m)^2)}$$

$$E = \frac{d^2 \times \cos(\theta)^3}{16 \times D^2}$$

In equations presented hereinabove, geometric spatial resolution is denoted by $R_g$; pinhole-to-center-of-image-matrix distance is denoted by po; pinhole-to-detector distance (or focal length) is denoted by pd; pinhole diameter is denoted by d; magnification at the center of image matrix is denoted by m; total spatial resolution is denoted by $R_o$; intrinsic spatial resolution of the detector is denoted by $R_i$; and the geometric efficiency of the collimator is denoted by E.

In some implementations of the present application, additional motor/motors can also be used for changing the tilt angle or for changing the pinhole-to-object distance and/or pinhole-to-detector distance to alter various features of the system.

Example 1

In this example, a set of Monte Carlo simulations was performed to assess the influence of tilt angle on image quality. The theoretical range for tilt angle in the application is 0°-90°. At tilt angle of 0°, the head is perpendicular to the imaging desk. In contrast, at 90° tilt angle, the head is parallel to the imaging desk. However, regarding the assumed sizes of the detector and the collimator (detector size of 30 cm (W)×30 cm (L)×⅜" (thickness), collimator thickness of 5 mm), to locate the head and collimator entirely below the imaging desk, the minimum tilt angle for retaining the head underneath the desk is about 30°. But the tilt angle of 0° and 15° were also simulated for better understanding of the effect of tilt angle on the image quality parameters. Furthermore, at a tilt angle of 90°, all projection views are the same and hence image reconstruction is not possible. So, in the assessment process, tilt angles ranging from 0° to 75° were analyzed. For all assessments, pinhole-to-center-of-image-matrix distance and pinhole-to-detector distance (focal length) were set to 18.75 mm and 300 mm, respectively. It should be understood by a person skilled in the art that any other set-up can be used to achieve different image quality.

Example 2

To evaluate the spatial resolution, 6 point sources of Technetium-99m (Tc-99m) were placed at different locations in the FOV, the details of which is presented and set forth in TABLE 2 herein below. It should be noticed that the center of image matrix was considered to be at the origin. Different sources are designated by numbers 1 to 6. All point sources contain the same value of activity. Also, all of them are ideal point sources i.e. they have no dimension.

TABLE 2

The positions of the 6 point sources scanned to assess spatial resolution.

| Sources | Cartesian coordinates (in mm) |
| --- | --- |
| Source #1 | (0, −5, −5) |
| Source #2 | (0, 0, −5) |
| Source #3 | (0, −5, 0) |
| Source #4 | (0, 0, 0) |
| Source #5 | (0, −5, 5) |
| Source #6 | (0, 0, 5) |

Data acquisition was performed using 16 views over 360° span. Each projection view was stored in a 512×512 matrix. Data were then reconstructed with an image voxel size of $(0.2 \text{ mm})^3$, using the dedicated image reconstruction code developed for the system via 3 iterations. Gaussian fitting was used to obtain the full-width at half-maximum (FWHM) of the reconstructed images of the point sources.

Figure 4:
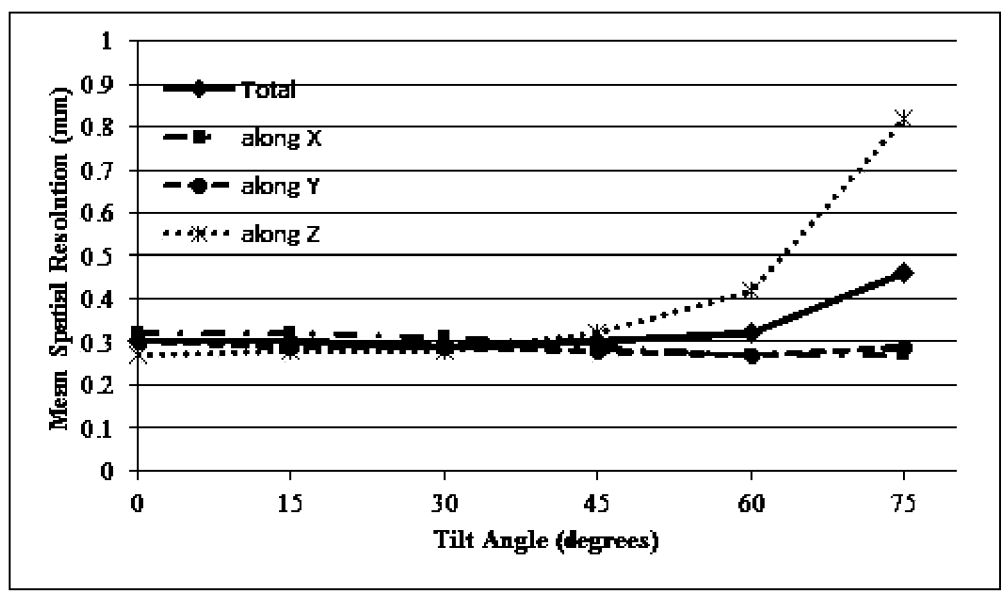
FIG. 4 Illustrates a plot of the mean spatial resolution (in terms of full-width at half-maximum (FWHM)) versus tilt angle measured using a set of 6 ideal point sources located at different positions in the field of view (FOV).

FIG. 4 of the DRAWINGS illustrates the mean spatial resolution along X, Y, and Z axes together with total spatial resolution as the average of spatial resolution along all the three axes. It should be noted that X-Y plane is parallel to the imaging desk and hence the Z axis is perpendicular to it. According to FIG. 4 of the DRAWINGS, the spatial resolution along all axes is about 0.3 mm for tilt angles less than 60°. Up to 45° tilt angle, total spatial resolution doesn't show any remarkable variations. Moreover, the total spatial resolution gets about 60% worse. Also, it can be seen that spatial resolution along all three dimensions (X, Y, and Z) are almost the same for tilt angles less than or equal to 45°.

Figure 5:
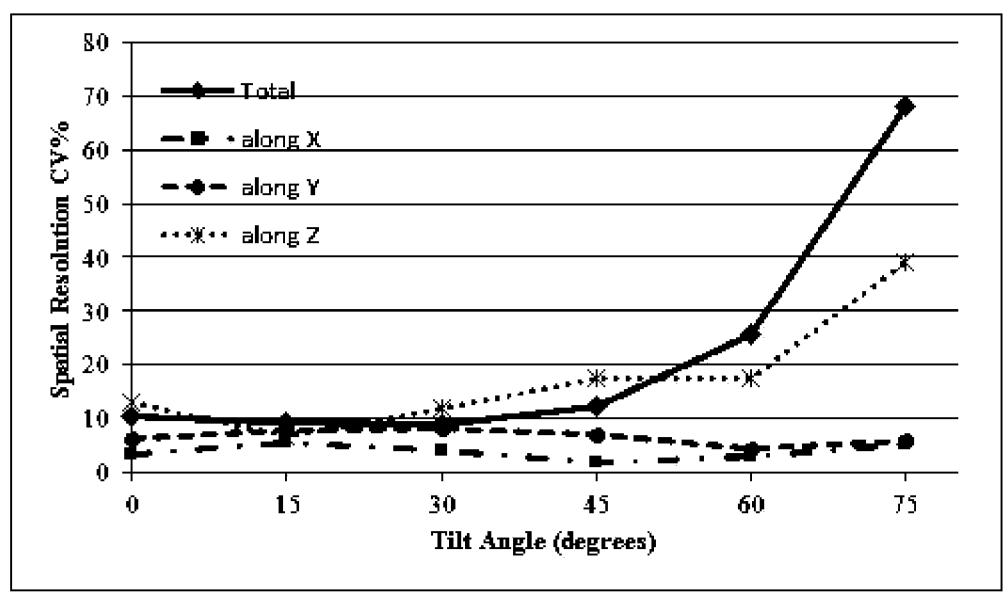
FIG. 5 Illustrates the percent coefficient of variation (CV %) of spatial resolution for the set of 6 ideal point sources located at different positions in the FOV.

FIG. 5 of the DRAWINGS reveals the percentage coefficient of variation (CV %) of the spatial resolution values as a measure of resolution uniformity through the FOV. As is observed, the CV % is in an appropriate level for tilt angles below 60°. Smaller values of CV % of spatial resolution and hence more uniform spatial resolution through the FOV, cause the various parts of an scanned object to be have the same spatial resolution in the reconstructed images.

Moreover, a sphere with a diameter of 10 mm was simulated with uniform activity of Tc-99m in 16 views over 360° span. Each projection view was stored in a 512×512 matrix. The images were reconstructed using 3 iterations with a voxel size of $(0.2 \text{ mm})^3$. The resultant images were used for calculating non-uniformity, noise, and normalized squared error (NSE) as a measure of similarity between the reference image and the reconstructed image.

For calculation of non-uniformity and noise, a volume of interest (VOI) as a sphere concentric with the main sphere but with a diameter of 7.5 mm was assumed. Noise was quantified using percentage standard deviation (STD %). NSE and non-uniformity was calculated using the following equations, respectively:

$$NSE = \frac{\sum_{n=1}^{N}(I(n) - I_{ref}(n))^2}{\sum_{n=1}^{N}(I_{ref}(n))^2}$$

$$\text{non\_uniformity}(\%) = 100 \times \frac{\max - \min}{\max + \min}$$

In the equations presented hereinabove, I is the reconstructed image matrix, $I_{ref}$ is the reference image matrix; n is the voxel index number, N is the total number of voxels in the matrix, max is the maximum, and min is the minimum values in the VOI.

For measuring the contrast, a sphere with a diameter of 10 mm is used as a background region and another concentric sphere with a diameter of 3 mm is used as a hot region, both of which were filled with Tc-99m. The activity concentration of the hot region was 4.7 times of that of the background, which leads to a maximum achievable contrast of 0.65. Data were acquired using 16 views over 360° span. Projection view data were stored in 512×512 matrices. Data were then reconstructed by 3 iterations with an image voxel size of (0.2 mm)³. Contrast was then calculated for each tilt angle using the following equation.

$$\text{Contrast} = \frac{mean_H - mean_{BG}}{mean_H + mean_{BG}}$$

In the equation presented hereinabove, $mean_H$ and $mean_{BG}$ denote the mean values of the hot and background regions, respectively.

Figure 6:
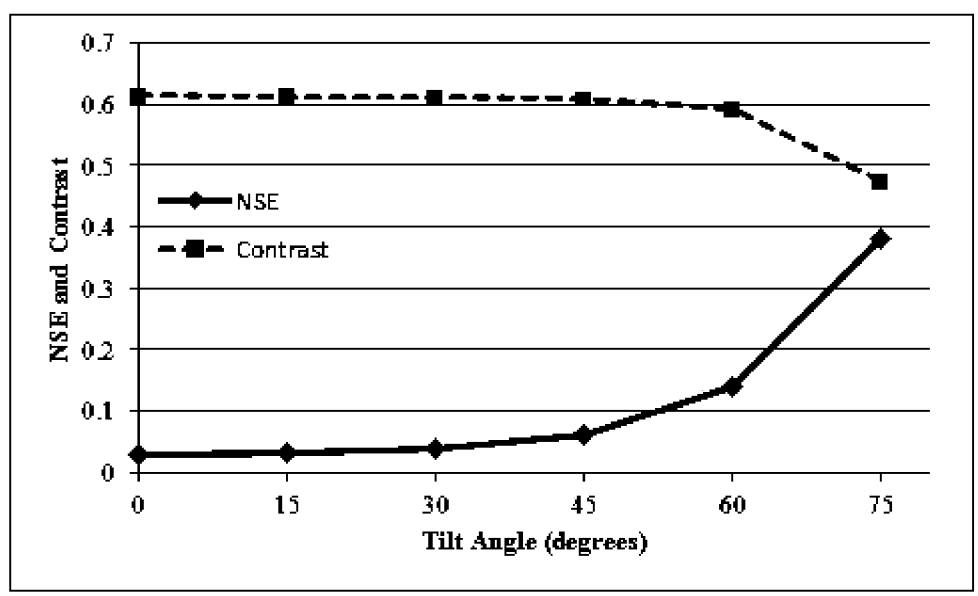
FIG. 6 Illustrates the Normalized Squared Error (NSE) and contrast in various tested tilt angles.

FIG. 6 of the DRAWINGS illustrates that NSE increases slightly while the tilt angle changes form 0° to 45°. However, its increase is much faster from 45° to 75°. FIG. 6 demonstrates, as well that contrast is almost constant with tilt angle change. But, it decreases at tilt angle of 75°.

Figure 7:
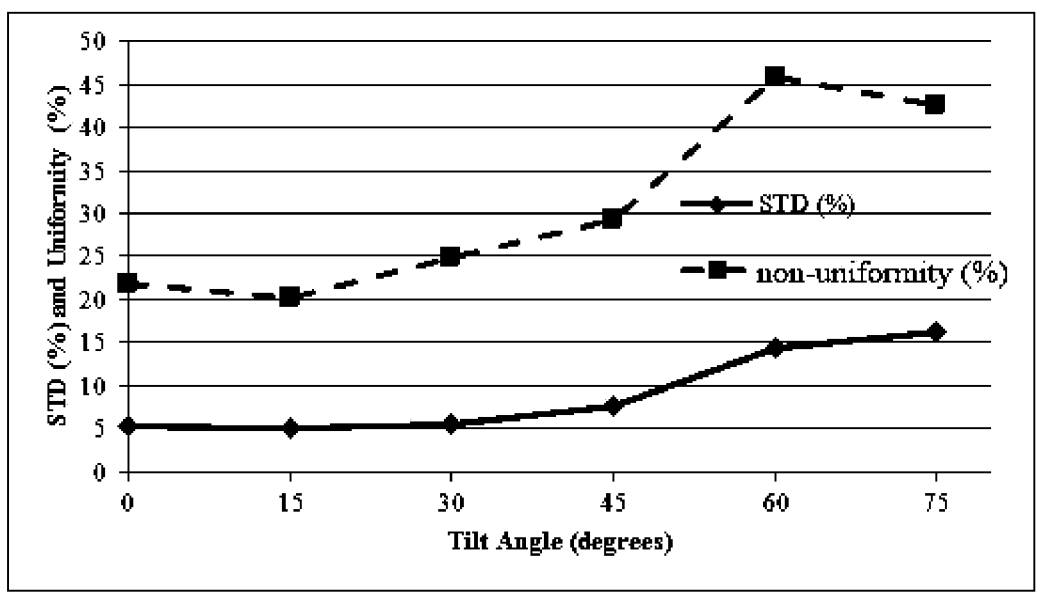
FIG. 7 illustrates the percent standard deviation and non-uniformity versus tilt angle measured using a 10 mm-diameter sphere with uniform activity.

According to FIG. 7 of the DRAWINGS, STD % is about 5% while tilt angle changes from 0° to 30°. It increases to about 16% at tilt angle of 75°. So, as a conclusion, using smaller tilt angles leads to less noisy images. However, non-uniformity has an overall increasing trend with increase of tilt angle. Similarly, from the non-uniformity point of view, smaller tilt angles lead to more uniform images.

Figure 8:
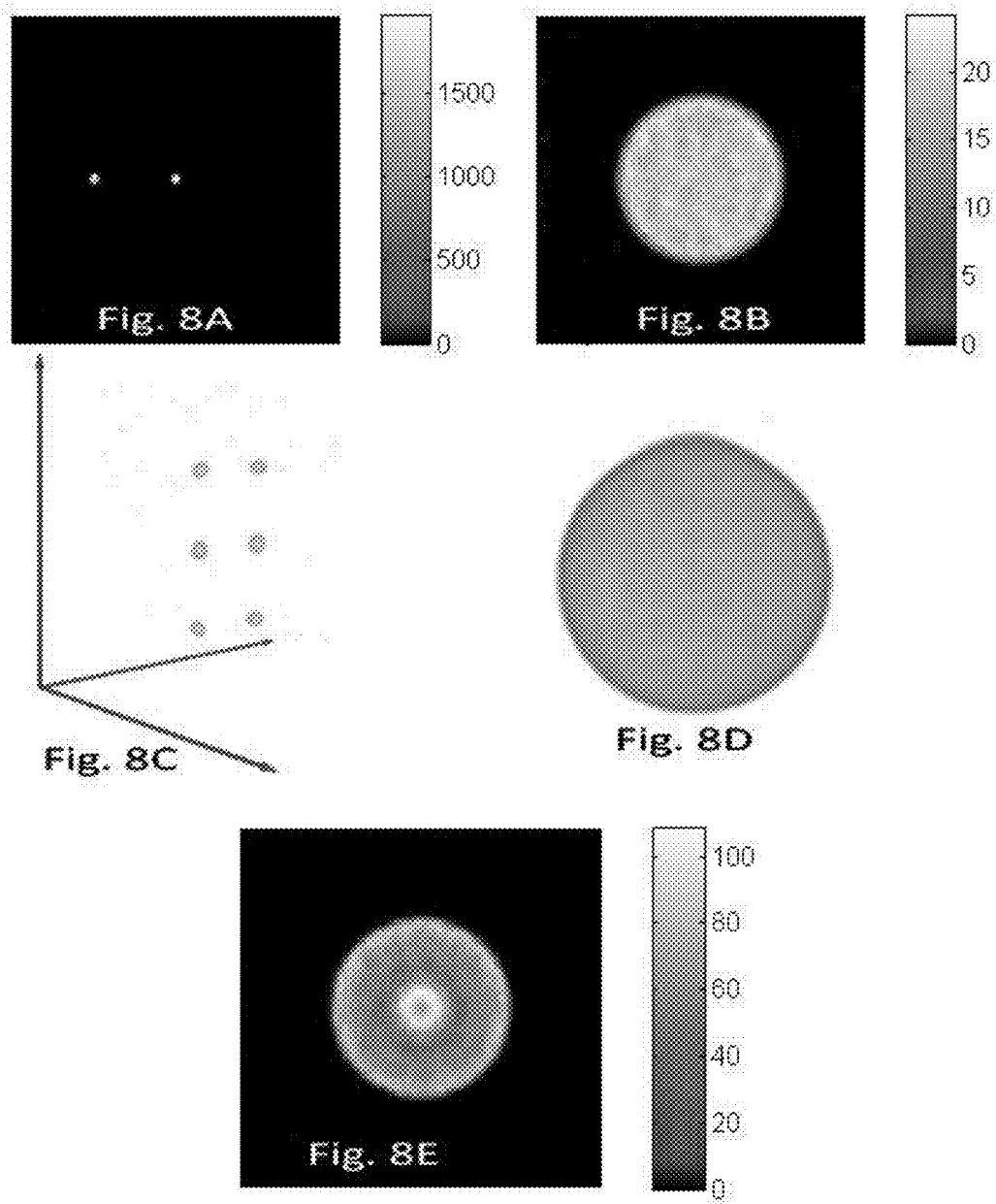
FIGS. 8A-E Illustrate sample slices of the reconstructed images of the set of point sources (FIG. 8A); sphere with uniform activity (FIG. 8B); 3D-rendered maximum intensity projection (MIP) images of the point sources (FIG. 8C); the sphere (FIG. 8D); and the middle slice of the reconstructed image of the contrast phantom (FIG. 8E).

With reference now to FIG. 8A and FIG. 8B, sample slices of the reconstructed images of the set of point sources and sphere with uniform activity are illustrated respectively. FIGS. 8C and 8D show the 3D-rendered MIP images of the point sources and the sphere, respectively, and FIG. 8E illustrates the middle slice of the reconstructed image of the contrast phantom at 30° tilt angle.

Based on the simulations performed and explained, some of the system performance parameters are summarized in TABLE 3. The tomographic spatial resolution of the system is about 0.3 mm. However, this value was obtained using MC simulation of ideal point sources. Practical measurements may differ slightly with this value. Moreover, variation of the spatial resolution through the FOV is about 9.0% in terms of CV % showing almost uniform spatial resolution in the whole FOV. Geometric efficiency of the system is about 0.02%. For calculation the total efficiency (or system efficiency), one should multiply the intrinsic efficiency of the detector applied to this value. Noise in terms of STD % is in the acceptable level of 5.6%. Non-uniformity also has an appropriate value of about 25%.

TABLE 3

| System performance parameters | |
| --- | --- |
| Tomographic spatial resolution | 0.3 mm |
| Geometric efficiency | 0.02% |
| Tomographic spatial resolution CV % throughout the FOV | 9.0% |
| Noise (in terms of STD %) | 5.6% |
| Non-uniformity (%) | 24.9% |

The data acquisition and image reconstruction parameters using the abovementioned set-up and tilt angle of 30°, at which the performance was assessed, as an exemplar implementation of the present application, are set forth in the TABLE 4.

TABLE 4

| Collimator, data acquisition, and image reconstruction parameters used as an example. | |
| --- | --- |
| Tilt angle | 30° |
| No. of projections | 16 |
| Angular span | 360° |
| Pinhole diameter | 1 mm |
| Collimator material | tungsten |
| Collimator thickness | 5 mm |
| Pinhole opening angle | 56° |
| Image voxel size | (0.2 mm)³ |
| No. of iterations | 3 |

Figure 9:
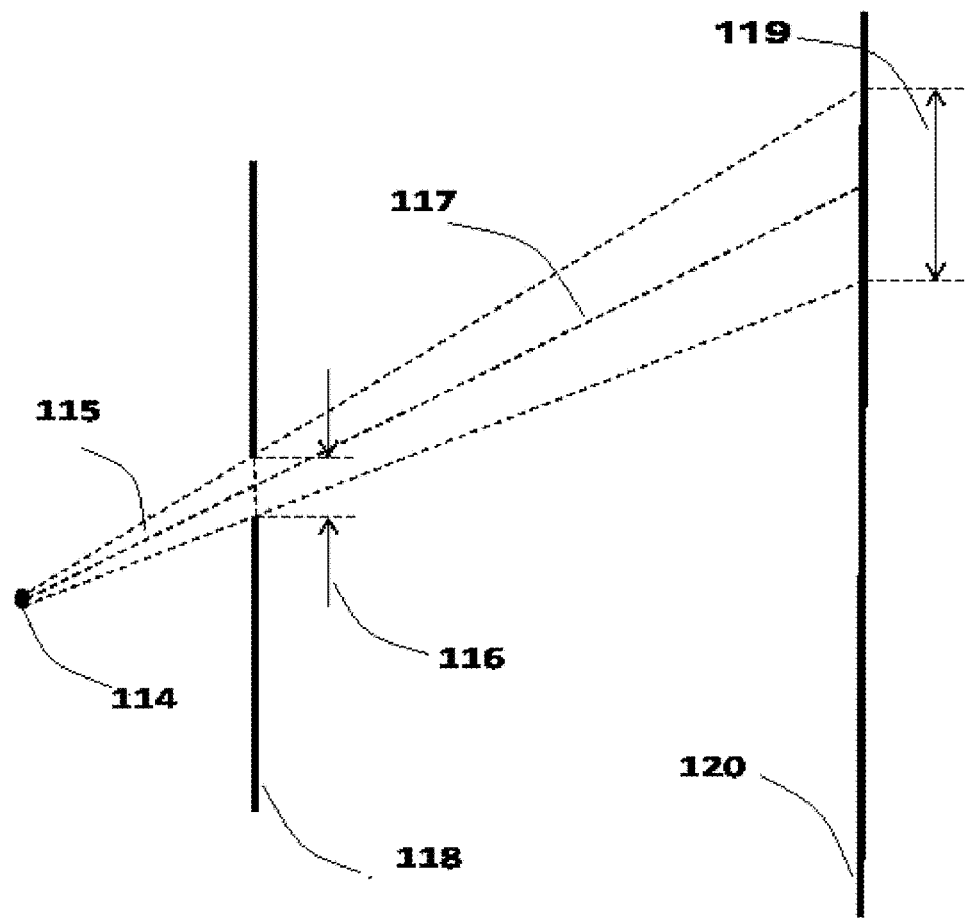
FIG. 9 illustrates cross sectional view of the projection of a typical image voxel through the pinhole when the collimator and the detector planes are parallel.

FIG. 9 of the DRAWINGS illustrates the path of the photons emitted from each voxel 114 toward the pinhole and form a cone passing the pinhole. The forward projection step finds the cross section of the cone with a detector plane 120, distributing each image voxel value to the detector bins related to the cross section, and finally calculating the superposition of the impact of all image voxels on the detector. With respect to the circular shape of the pinhole and the fact that the collimator plane 118 and the detector plane 120 are parallel to each other, it can be shown that the cross section of a given cone, whose apex is one of the image voxels passing through the pinhole, is a circle on the detector plane 120. The location of the circle on the detector plane 120 as well as its diameter 119 can be analytically obtained. The diameter of the circle 119 is computed using the following equation:

$$D = \frac{h+H}{h} \times d_{re}$$

In the abovementioned equation, diameter of circle 119 is denoted by D, voxel-to-pinhole distance 115 is denoted by h, pinhole-to-detector distance 117 is denoted by H, and the resolution-related effective diameter of the pinhole 116 is denoted by $d_{re}$. The resolution-related effective diameter of the pinhole 116 is calculated using the following equation:

$$d_{re} = d \times \left(1 - \ln(0.5) \times \frac{\tan\left(\frac{\alpha}{2}\right)}{\mu \times d}\right)$$

In the equation presented hereinabove, μ and α denote linear attenuation coefficient of the collimator and opening angle of the pinhole, respectively. The value of the image voxel is then distributed to the detector bins which are covered by the corresponding circle.

Superposition of the projection of all image voxels on the detector forms the forward projection of the whole image. The process of comparison of the forward-projected data with the measured projection data is performed by simple calculation leading to an error matrix. The error matrix is then back-projected to update the previous estimate image. Since in this example data is acquired using 16 views, full iteration in image reconstruction algorithm consists of 16 sub-iterations. Depending on the distribution of the activity in the object, which is scanned, some iteration is needed to reach an appropriate estimate of the activity distribution by image reconstruction algorithm.

While the present application has been illustrated by the description of the implementations thereof, and while the implementations have been described in detail, it is not the intention of the applicant to restrict or in any way limit the scope of the appended claims to such detail. Additional advantages and modifications will readily appear to those skilled in the art. Therefore, the application in its broader aspects is not limited to the specific details, representative apparatus and method, and illustrative examples shown and described. Accordingly, departures may be made from such details without departure from the breadth or scope of the applicant's concept. Furthermore, although the present application has been described in connection with a number of exemplary implementations, the present application is not so limited but rather covers various modifications and equivalent arrangements, which fall within the purview of the appended claims.

What is claimed is:

1. A single-photon emission computed tomography (SPECT) imaging system comprising:
    an imaging desk located in a first plane; and
    a head located below the imaging desk and configured to rotate around an object to be imaged, wherein:
        the head is coupled to a motor and includes a detector and a collimator,
        the head is configured to rotate in a second plane parallel to the first plane, and
        the head is tilted under the imaging desk with a tilt angle being in a range of 0° to 90°.

2. The SPECT imaging system according to claim 1, wherein the system has a desktop open-gantry structure.

3. The SPECT imaging system according to claim 1, wherein the collimator is selected from a group consisting of parallel-hole, pinhole, multi-pinhole, and combination thereof.

4. The SPECT imaging system according to claim 1, wherein the collimator includes a pinhole collimator.

5. The SPECT imaging system according to claim 1, wherein the collimator is made of lead, tungsten or gold.

6. The SPECT imaging system according to claim 1, wherein the detector is selected from a group consisting of simple monolithic scintillation crystal coupled to Photomultiplier Tubes (PMTs), a pixelated scintillating crystal coupled to Position-Sensitive PMTs (PSPMTs), a monolithic/pixelated crystal coupled to photodiodes, or a solid-state detector.

7. The SPECT imaging system according to claim 1, wherein the detector includes a monolithic scintillation crystal coupled to PMTs.

8. The SPECT imaging system according to claim 1, wherein whole parts of the object to be imaged are placed on the imaging desk.

9. The SPECT imaging system according to claim 1, wherein a first portion of the object to be imaged is placed on the imaging desk and a second portion of the object is placed beneath the imaging desk.

10. A method for data acquisition in a SPECT imaging system, wherein the SPECT imaging system has an open-gantry structure and includes an imaging desk and a head located below the imaging desk and configured to rotate around an object to be imaged, the method comprising:
    placing the object on or beneath the imaging desk located in a first plane;
    rotating the head around the object while the head is tilted underneath the imaging desk;
    acquiring a plurality of projection views of the object; and
    storing the acquired projection views, wherein:
        rotating the head around the object includes rotating the head in a second plane spaced apart from the first plane and parallel to the first plane.

11. The method according to claim 10, wherein the head includes a detector and a collimator.

12. The method according to claim 11, wherein the collimator is selected from a group consisting of parallel-hole, pinhole, multi-pinhole and combination thereof.

13. The method according to claim 11, wherein the collimator includes a pinhole collimator.

14. The method according to claim 11, wherein the detector is selected from a group consisting of simple monolithic scintillation crystal coupled to Photomultiplier Tubes (PMTs), a pixelated scintillating crystal coupled to Position-Sensitive PMTs (PSPMTs), a monolithic/pixelated crystal coupled to photodiodes, or a solid-state detector.

15. The method according to claim 11, wherein the detector includes a monolithic scintillation crystal coupled to PMTs.

16. The method according to claim 10, wherein the object includes a human organ.

17. The method according to claim 10, wherein the object includes a part of human body or an animal.

18. The method according to claim 10, wherein the object is placed beneath the imaging desk.

19. The method according to claim 10, wherein the head is tilted under the imaging desk with a tilt angle, and the tilt angle is between 0° to 90°.

20. A method of obtaining a 3-D map of activity concentration in a SPECT imaging system, wherein the SPECT imaging system has an open-gantry structure and includes an imaging desk and a head located below the imaging desk and configured to rotate around an object to be imaged, the method comprising:
    placing the object on or beneath the imaging desk resting in a first plane;
    rotating the head around the object while the head is tilted underneath the imaging desk;
    acquiring a plurality of 1-dimensional or 2-dimensional projection views of the object;
    storing the plurality of projection views; and
    performing a tomographic reconstruction algorithm for calculation of a 3-D map of activity concentration from the plurality of projection views, wherein:
        rotating the head around the object includes rotating the head around the object in a second plane parallel to the first plane.

* * * * *